United States Patent [19]

Gergely

[11] 4,446,370
[45] May 1, 1984

[54] APPARATUS FOR DETECTING OIL IN WATER

[75] Inventor: John S. Gergely, Ponca City, Okla.

[73] Assignee: Conoco Inc., Ponca City, Okla.

[21] Appl. No.: 334,596

[22] Filed: Dec. 28, 1981

[51] Int. Cl.³ .......................... G08B 21/00; G08B 1/08
[52] U.S. Cl. .................................. 250/301; 73/170 A; 340/605; 364/420
[58] Field of Search ................ 250/301, 255; 364/418, 364/420; 340/600, 605; 73/170 A

[56] References Cited

U.S. PATENT DOCUMENTS

| 3,501,639 | 3/1970 | Monroe . | |
|---|---|---|---|
| 3,736,428 | 5/1973 | Monroe . | |
| 3,747,405 | 7/1973 | Fort et al. | 73/170 A |
| 3,760,362 | 9/1973 | Copland et al. | 364/420 |
| 3,842,270 | 10/1974 | Gregory . | |
| 3,899,213 | 8/1976 | Fantasia et al. . | |
| 3,961,187 | 6/1976 | Barringer . | |
| 4,001,764 | 1/1977 | Holland et al. | 73/170 A |
| 4,034,219 | 7/1977 | Louden et al. | 250/301 |
| 4,043,180 | 8/1977 | Morris et al. | 340/605 |
| 4,058,802 | 11/1977 | Meyers | 340/605 |
| 4,178,512 | 12/1979 | Frungel et al. . | |

OTHER PUBLICATIONS

Frungel and Koch, "Practical Experience with the Variosens Equipment in Measuring Chlorophyll Concentrations and Fluorescent Tracer Substances, Like Rhodamine, Fluorescein, and Some Substances," IEEE Journal of Oceanic Engineering, vol. OE-1, No. 1, Sep. 1976, pp. 21-32.

Variosens Brochure of Impulsphysics U.S.A., Inc.

Primary Examiner—Alfred E. Smith
Assistant Examiner—T. N. Grigsby
Attorney, Agent, or Firm—William J. Miller

[57] ABSTRACT

Apparatus for detecting oil in water. A plurality of oil sensors are maintained at selected positions in a body of water. Each sensor includes a limited wavelength light source for inducing fluorescence in oil which may be present and a light detector for detecting such induced fluorescence. Each sensor is connected to a computer which receives and stores information generated by each light detector.

12 Claims, 4 Drawing Figures

APPARATUS FOR DETECTING OIL IN WATER

BACKGROUND AND SUMMARY OF THE INVENTION

The instant invention relates to oil monitoring apparatus and more particularly to such apparatus which monitors oil in water.

In the past, various oil monitoring apparatus have been proposed which incorporate a limited wavelength light source that emits light of the frequency that makes oil fluoresce. A light detector generates a signal responsive to the amount of fluorescence induced in oil which may be present. One such past monitor employs a large housing through which falls a stream of water in which oil is to be detected.

Another such monitor is constructed to be suspended on a cable from a boat for detection of oil under water at depths up to around 1,000 meters. The light detector in the monitor provides a signal on the cable which is related to the amount of fluorescence induced in oil which may be present. The signal is provided to a meter in the boat which indicates the amount of oil that the monitor is detecting.

None of the past monitors are suitable for certain situations in which it is desirable to detect oil in water. For example, none of the past monitors are suitable for real-time monitoring of large underwater areas. One such situation in which real-time monitoring of a large underwater area is desirable is along an underwater oil pipeline.

Oil pipelines may be located on or buried in the floor of a body of water. For example, when oil is produced from an offshore well, a pipeline is typically provided to transport the oil from the well to the shore. It is desirable to monitor the water along the pipeline for the presence of oil to determine whether or not the pipeline is leaking. Neither of the above-discussed oil monitors are suitable for this purpose. The volume of water to be monitored prevents efficient use of the monitor which is designed to be suspended from a boat. The other above-discussed monitor is not useable for monitoring oil under water.

It is an object of the present invention to provide a method and apparatus for monitoring the presence of oil in large underwater areas.

It is another object of the present invention to provide such a method and apparatus which achieves such monitoring on a real-time basis.

It is a more specific object of the present invention to provide such a method and apparatus in which a computer stores real-time information relating to the amount of oil in the water being monitored.

It is yet another object of the present invention to provide such a method and apparatus which performs the monitoring in a substantially automatic fashion.

The instant invention includes a plurality of oil sensors each of which is contained in a cylindrical housing. The sensors are of the type having a limited wavelength light source for inducing fluorescence from oil which may be present. A light detector detects any resulting fluorescence. Each sensor is maintained under water in a selected position. Each of the sensors is connected to a computer which receives and stores information generated by each light detector to provide a real-time map of the amount of oil in the monitored water.

These and other objects and attendant advantages of the invention will become more fully apparent as the following detailed description is read in view of the accompanying drawings.

DETAILED DESCRIPTION OF THE INVENTION

Figure 1:
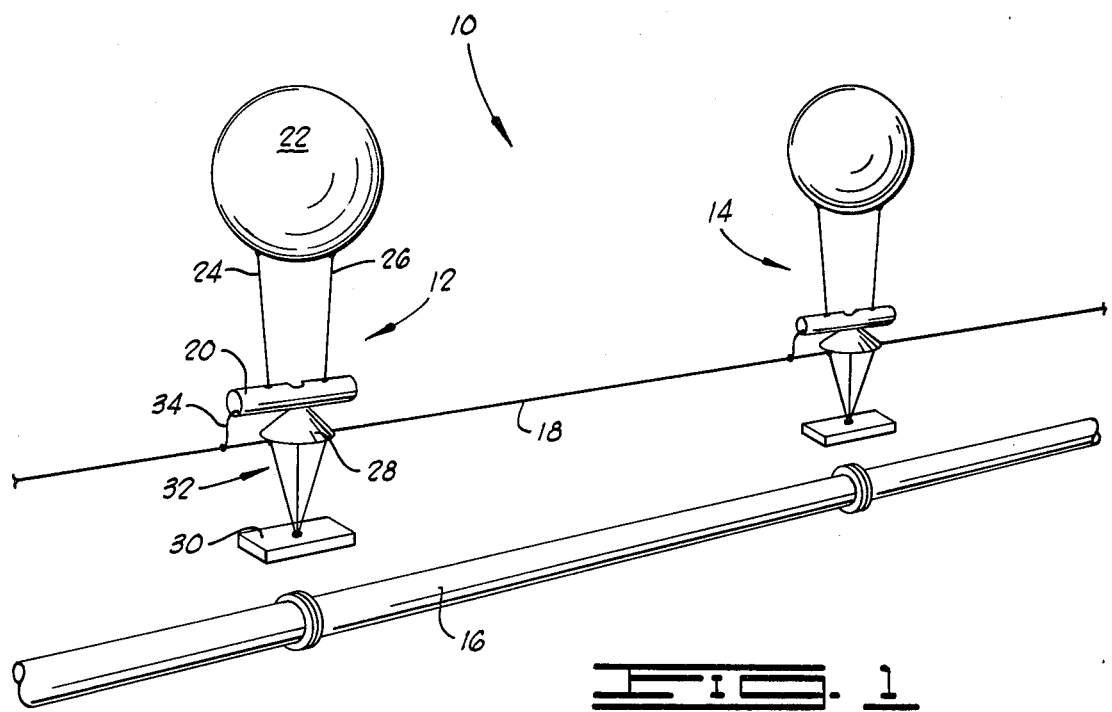
FIG. 1 is a perspective view of a portion of the instant embodiment of the invention.

Indicated generally at 10 in FIG. 1 is a portion of the instant embodiment of the invention. Included therein are sensing stations, indicated generally at 12, 14. Each of the stations is positioned under water over an oil pipeline 16.

Speaking only generally of the structure and operation of the instant embodiment of the invention, a plurality of sensing stations, like sensing stations 12, 14, are suspended along pipeline 16. Each station includes a limited wavelength light source which emits light at a frequency that makes oil fluoresce. A light detector located at each station generates a signal related to the level of induced fluorescence and hence the amount of oil detected. Each detector signal is placed on a cable 18 which transmits all of the signals to a computer for storage and processing.

Examining in more detail the structure of sensing station 12, a cylindrical detection chamber 20 is buoyed upwardly by a balloon 22 attached to the top of the chamber by cords 24, 26. A funnel 28 is mounted on the bottom of the chamber and a weight 30 is suspended from the lower portion of funnel 28 by cords indicated generally at 32. An electronics cable 34 connects electrical components (to be later more fully explained) in chamber 20 to cable 18.

Figure 2:
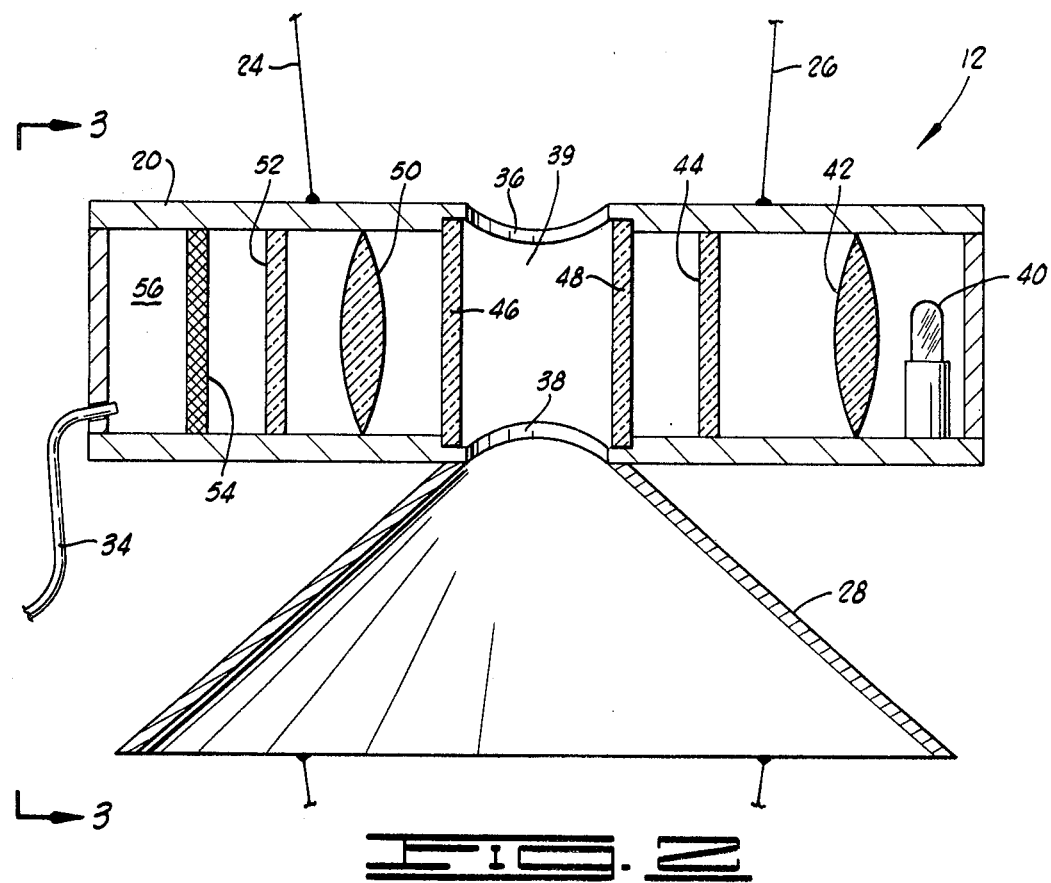
FIG. 2 is a cross-sectional view of one of the sensors of the instant embodiment of the invention.
Figure 3:
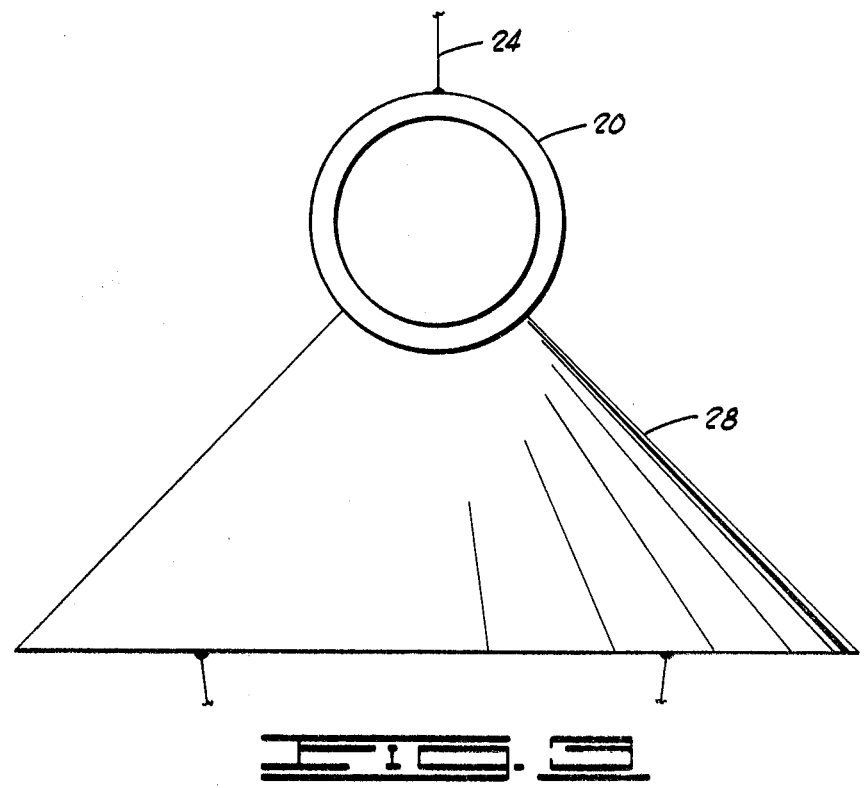
FIG. 3 is a full view taken along line 3—3 in FIG. 2.

It is to be appreciated that the instant embodiment of the invention includes a plurality of sensing stations suspended along pipeline 16 and connected to cable 18, as are stations 12, 14. For a more detailed view of station 12, attention is directed to FIG. 2.

Bores 36, 38 are provided in opposing portions of chamber 20. The bores provide a fluid flow path from the inside of funnel 28 through bore 38 into a water sampling chamber 39 and out of bore 36.

A lamp 40 is mounted on the inside of detection chamber 20 at one end. Alternatively, a light emitting diode may be used in place of lamp 40. The lamp, when energized, emits a wide band spectral output. A conventional collimating lens 42 is circularly shaped and is mounted on the interior of chamber 20 about its circumference. A conventional circular interference filter 44 is likewise mounted about its circumference inside chamber 20. Filter 44 is of the type which permits light passage only of a selected wavelength range. In the instant embodiment of the invention, filter 44 permits passage of a band width of approximately 10 nanometers (nm) at a wavelength centered about 500 nm. It has been found that light passed by filter 44 is of the optimum wavelength for exciting fluorescence in oil, while at the same time reducing unwanted fluorescence from interfering substances such as algae, bacteria, and Raman signals from water.

A pair of circular transparent quartz windows 46, 48 are mounted on shoulders which extend about the circumference of cylinder 20 on either side of bores 36, 38.

A second collimating lens 50 is mounted on the interior of chamber 20 in the same manner as collimating lens 42. Collimating lenses 42, 50 are substantially identical and, as will later be more fully explained, perform similar functions. A second interference filter 52 is mounted on the interior of chamber 20 in the same manner as filter 44; however, filter 52 is constructed to band pass light in the 510 to 560 nanometer wavelength range. This includes substantially all of the spectrum of oil fluorescence, which has been induced by an exciting light wavelength of approximately 500 nanometers.

A silicon photodiode 54 is mounted on the inside of chamber 20 adjacent filter 52. Diode 54 generates an electrical signal which is related to the amount of light that strikes the surface of the diode. Diode 52 is connected to electronics (not shown in FIG. 2) contained in space 56 between diode 54 and the end of chamber 20. As will be recalled, cable 34 connects components in cylinder 20 to cable 18. For a view of the components contained in space 56 as well as the connections of cable 34 to structure in chamber 20, attention is directed to FIG. 4.

Figure 4:
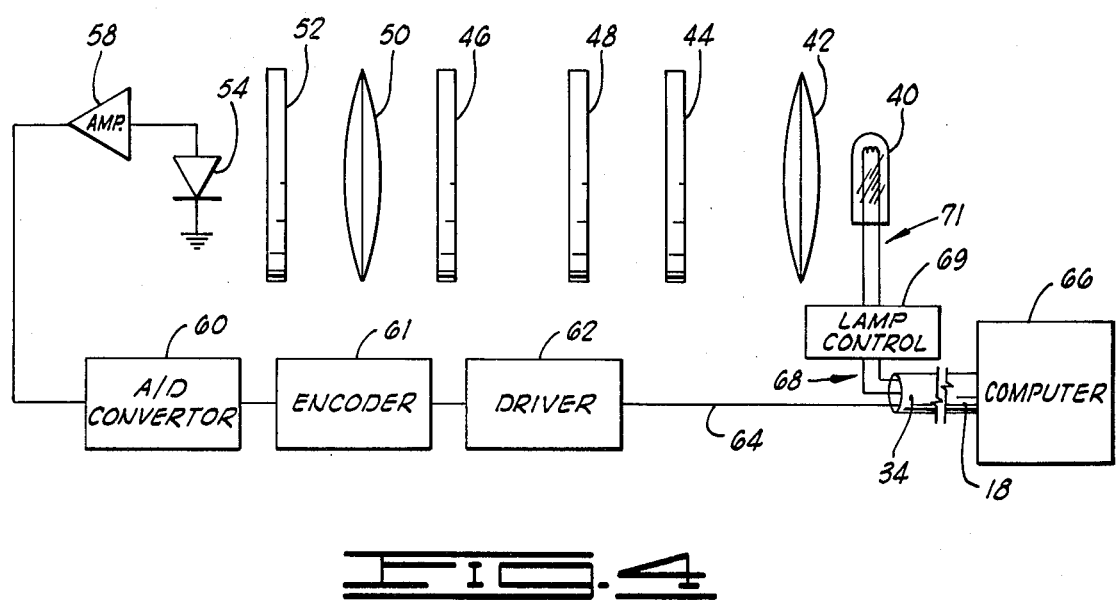
FIG. 4 is a partially schematic view of a portion of one of the sensors of the instant embodiment of the invention.

Structure which has been previously identified is correspondingly numbered in FIG. 4. Additional structure, which is contained in space 56 in chamber 20, includes a conventional amplifier 58. A signal generated by diode 54 is applied to the input of the amplifier which amplifies the signal. The amplified signal is applied to the input of an analog-to-digital converter 60. Converter 60 is of conventional construction and serves to convert the analog signal applied to its input into a binary digital signal, which signal is applied to the input of an encoder 61.

Encoder 61 is a conventional digital circuit which generates a unique digital number that is applied to the input of a driver 62 along with the binary information generated by converter 60. Thus, the digital information generated by the converter, which relates to the signal level of diode 54, is associated with a unique digital number generated by the encoder. Each of the sensing stations includes an encoder, like encoder 61; however, each station's encoder generates and tags its binary information with a different digital number so the detected signal can be associated with the sensing station from which it was generated.

In the instant embodiment of the invention, driver 62 is a power amplifier. The driver, as well as amplifier 58, converter 60, and encoder 61 are contained within space 56. The output of driver 62 is applied to a conductor 64 which exits chamber 20 in cable 34. As will be recalled, cable 34 connects the electronics in the chamber to cable 18. Each of the other sensing stations includes a conductor, like conductor 64, and an electronics cable, like cable 34. A conventional power supply (not shown) provides a source of voltage in the usual manner to the electronic components in chamber 20.

Each of the conductors are connected to cable 18 which is connected at one end to a computer 66. Each of the drivers, like driver 62 in station 12, serves to provide the binary signals generated by the stations converter with sufficient power so that it may be transmitted along the cable to the computer.

A pair of conductors, indicated generally at 68, connect a lamp control circuit 69 to the computer via cable 34 and cable 18. The lamp control circuit resides in space 56 and is connected to the previously mentioned power supply (not shown). A pair of conductors, indicated generally at 69, connect the lamp control circuit to lamp 40. Each of the other sensing stations include a lamp control circuit connected to its associated lamp. Included in computer 66 (not shown) are controls which can selectively signal each station's lamp control circuit to instruct it to energize its associated lamp.

In operation, each of the sensing stations along the pipeline is maintained in its vertical position by virtue of its associated balloon and weight, like balloon 22 and weight 30 at station 12. Each station is restrained from substantial movement in a horizontal plane since it is connected to cable 18 with its associated electronics cable.

When lamp 40 is energized in station 12 pursuant to a signal generated by the controls in computer 66, light from the lamp passes through collimating lens 42. Lens 42 collimates the light rays from lamp 40 before they strike interference filter 44. This collimation enables filter 44 to effectively filter out light at other than an approximately 10 nanometer band width centered at 500 nanometers. The band width limited light passes through quartz window 48 into the water which flows through funnel 28 and bores 36, 38. The funnel serves to entrain water from a broad volume of water about the sensing station for passage through bores 36, 38. Natural motion of chamber 20 in the water aids the passage of water through the area between quartz windows 46, 48 (referred to herein as water sampling chamber 39).

In the event that oil is present in the water between the windows, the light passing therethrough induces fluorescence in the oil. Such fluorescent light passes through window 46, through collimating lens 50 (which serves the same function as lens 42) and through interference filter 52. As will be recalled, filter 52 is constructed to pass only the spectra emitted by the light of oil fluorescing. When such light passes through the filter, it strikes photodiode 54 which generates a signal that is related to the amount of fluorescence (and hence the amount of oil). The signal is amplified by amplifier 58, converted into digital form by converter 60 and encoded by encoder 61. Driver 62 amplifies the encoded binary signal and transmits it via cable 34 and cable 18 to computer 66. Since the encoder has tagged the signal information generated by photodiode 54 with a unique number, the computer associates the signal information with a sensor location.

It is to be appreciated that the above-described process in station 12 occurs in each of the other stations as well, thus enabling the computer to pinpoint an area of leakage from the pipeline and to create a map of oil in the water along the pipeline.

Depending upon desired operation, the computer may maintain each of the lamps in the sensing stations in a continuously-on condition thereby enabling continuous real-time monitoring for oil pollution covering the monitored area. Alternatively, also under computer control, the lamps may be pulsed at periodic intervals to enable the computer to sample the level of oil pollution in the monitored area.

Modifications and additions may be made to the above-described embodiment of the invention without departing from the spirit and scope of the invention which is defined in the following claims.

I claim:

1. An apparatus for detecting oil in water comprising:

a plurality of oil sensors of the type having a limited wavelength light source for causing florescence of oil which may be present in the water, and having a light detector to detect resulting florescence;

means including suspension means attached to each of said sensors for maintaining each sensor at a selected position in the water;

computer means; and, means for connecting each sensor to said computer means to permit said computer to receive and store information generated by each light detector.

2. The apparatus of claim 1 wherein suspension means includes a balloon.

3. The apparatus of claim 1 wherein each sensor is housed in a cylindrical detection chamber having a funnel extending downwardly therefrom.

4. The apparatus of claim 1 wherein said computer means includes control means for selectively energizing said light sources.

5. The apparatus of claims 1 or 4 wherein each of said sensors includes unique identification means to permit said computer to associate such generated information with a sensor location.

6. An apparatus for detecting oil leaks along an oil pipeline submerged in a body of water, said apparatus comprising:

a plurality of water sampling chambers suspended at selected intervals over said pipeline;

a limited-wavelength light source for each chamber, each source being positioned to direct light into its associated chamber and being constructed to emit light of the wavelength that makes oil fluoresce;

a light detector for each chamber, each detector being positioned to detect fluorescence in its associated chamber and being constructed to generate a signal containing information relating to detected fluorescence;

computer means; and means for connecting each detector to said computer means to permit said computer to store said signals.

7. The apparatus of claim 6 wherein said connecting means further includes means for connecting each light source to said computer means to permit said computer to selectively energize said light sources.

8. The apparatus of claim 6 which further includes a cylindrical casing having said light source at one end, said light detector at the other end and said chamber positioned between said source and said detector.

9. The apparatus of claim 8 wherein said casing has formed therein opposing openings into said chamber and funnel means are mounted on said casing over one of said openings.

10. The apparatus of claim 8 wherein said casing further includes unique identification means to permit said computer to associate detector signals with a casing location.

11. A method for detecting oil leaks from an oil pipeline submerged underwater comprising the steps of:
(a) providing a plurality of oil sensors suspended adjacent the pipeline along its length, said sensors being of the type having an oil-fluorescing light source and a detector for generating signals relating to oil fouorescence;
(b) energizing the light sources;
(c) measuring the signals generated by each detector;
(d) relating the signals generated by each detector to a sensor location to create a map of oil in the water along the pipeline.

12. The method of claim 11 which further includes the steps of turning off the light source and repeating steps (b) through (d) at periodic intervals.

* * * * *